US006355469B1

(12) United States Patent
Lam

(10) Patent No.: US 6,355,469 B1
(45) Date of Patent: Mar. 12, 2002

(54) **NUCLEIC ACID ENCODING *M. TUBERCULOSIS* ALGU PROTEIN**

(75) Inventor: Kelvin T. Lam, Belmont, MA (US)

(73) Assignee: Anadys Pharmaceuticals, Inc., Waltham, MA (US)

(*) Notice: Subject to any disclaimer, the term of this patent is extended or adjusted under 35 U.S.C. 154(b) by 0 days.

(21) Appl. No.: 09/082,920

(22) Filed: Jan. 16, 1998

Related U.S. Application Data

(60) Provisional application No. 60/035,391, filed on Jan. 16, 1997.

(51) Int. Cl.[7] .............................. C12N 1/20; C12N 9/12

(52) U.S. Cl. ........................ 435/252.3; 435/6; 435/183; 435/194; 435/419; 435/325; 435/254.11; 435/320.1; 435/348; 536/23.1; 536/23.2; 536/23.7; 530/350

(58) Field of Search ............................ 435/6, 325, 194, 435/419, 348, 183, 254.11, 320.1, 252.3; 530/350; 536/23.2, 23.1, 23.7

(56) References Cited

PUBLICATIONS

DeMaio et al. A stationary–phase stress–response sigma factor from *Mycobacterium tuberculosis*, Proc. Natl. Acad. Sci. USA 93:2790–2794, Apr. 1996.*

Collins et al., *Proceedings of the National Academy of Science*, 92:8036–8040, 1995.

Lonetto et al., *Proceedings of the National Academy of Science*, 91:7573–7577, 1994.

Hiratsu, et al. (1995) *J.Bacteriol.* 177:2918–2922.

Cirillo et al. (1994) *Mol.Microbiol.* 11:629.

Cooksey et al. (1993) *Antimicrob.Agents. Chemother.* 37:1348.

Curcic et al. (1994) *Mol.Microbiol.* 13:1057.

Das Gupta et al. (1993) *J.Bacteriol.* 175:5186.

Dhadayuthap et al. (1995) *Mol.Microbiol.* 17:901.

Jacobs, W.R. et al., (1986) "In vivo repackaging of recombinant cosmid molecules for allayses of *Salmonella typhimurium, Streptococcus mutants*, and Mycobacterial Genomic libraries". *Infect. Immun.* 52:101–109.

Ji et al. (1994) *Microbiol.* 140:2829.

Kong, et al. (1993) *Proc.Natl.Acad.Sci.USA* 90:2608.

Kremer (1995) *J. Bacteriol.* 177:642.

Malakooti et al. (199 ) *J.Bacteriol.* 177:6854.

Murray et al. (1992) *Mol. MicObiol.* 6:3331.

Novick, R. (1996) "Mycobacteria: Growth, Metabolism, and Molecular Biology". *Tuberculosis* (Little, Brown, and Co., Boston, MA) pp 187–198.

Stover et al., (1991) *Nature* 351:456.

Silhavy et al. (1985) *Microbiol. Rev.* 49:398.

Tang, H., et al., (1995) "Rapid RNA polymerase genetics: One–day, no–column preparation of reconstituted recombinant *Escherichia coli* RNA polymerase". *Proc. Natl. Acad. Sci. USA* 92:4902–4906.

Weiden, M. et al., (1996) "Genetics of *M. tuberculosis*". In *Tuberculosis* (Little, Brown, and Co., Boston, MA) pp 211–222.

Yura and Ishihama (1979) Genetics of bacterial RNA polymerases. *Ann. Rev. Genet.* 13:59–97.

Vall–Spinosa, A. et al., *N. Engl. J. Med.* 283;616–621, 1970.

Zalenskaya, K. et al., *Gene* 89:7–12.

Deretic, V., M. Schurr, J. Boucher, and D. Martin. (1994) Conversion *Pseudomounus aeruginosa* mucoidy in cystic fibrosis: environmental stress and regulation of bacterial virulence by alternative sigma factors. *J Bacteriol* 17: 2773–2780.

Kashlev, M., Martin, E., Polyakov, A., Severinov, K., Nikiforov, V., and Goldfarb, A. (1993) Histidine–tagged RNA polymerase: dissection of the transcription cycle using immobilized enzyme. Gene 130: 9–14.

Martin, D., M. Scurr, M. Mudd, J. Govan, B. Holloway, and V. Deretic (1993) *Proc. Natl. Acad. Sci.* 90: 8377–8381.

Miller, L., Crawford, J.T., and Shinnick, T.M. (1994) The rpoB gene of *Mycobacterium tuberculosis*. Antimicrob. Agents. Chemo. 38: 8085–811.

Philipp, W.J., Poulet, S., Eiglmeier, K., Pascopella, L., Balasubramanian, V., Heym, B., Bergh, S., Bloom, B.R., Jacobs, W.R., and Cole, S.T. (1996) Proc. Natl. Acad. Sci. USA 93: 3132–3137.

Raina, S., D.Missiakas, and C. Geogopoulos. (1995) The rpoE encoding the $\sigma^{E(\sigma 24)}$ heat shock sigma factor of *Escherichia coli. EMBO J* 14: 1043–1055.

Rouvier, P., A. De Las Penas, C. Lu, K. Rudd, and C. Gross. (1995) rpoE the gene encoding the second heat–shock sigma factor, $\sigma^E$, in *Escherichia coli. EMBO J* 14: 1032–1042.

Schurr, M.J., H. Yu., J.M. Martinez–salazar, J.C. Boucher and V. Deretic. (1996) Control of algU, a member of the $\sigma^E$–like family of stress sigma factors, by the negative regulators mucA and mucB and *Pseudomonas aeruginosa* conversion to mucoidy in cystic fibrosis. *J. Bacteriol* 178:4997–5004.

Erickson, J.W., and C.A. Gross. (1989) Identification of the sigma subunit of *Escherichia coli* polymerase: a second sigma factor involved in high–temperature gene expression. Genes Dev. 3:1462–1471.

Lipnska, B., S. Sharma, and C. Georgopoulos. (1988) Sequence analysis and regulation of the htrA gene of *Escherichia coli*: a $\sigma^{32}$–independent mechanism of heat–inducible transciption. Nucleic Acids Res. 16:10053–10067.

Martin, D.W., M.J. Schurr, H. Yu, and V. Deretic. (1994) Analysis of promoters controlled by the putative sigma factor AlgU regulating conversion to mucoidy in *Pseudomonas aeruginosa*: relationship to stress response. J. Bacteriol. 176:6688–6696.

(List continued on next page.)

*Primary Examiner*—Rebecca E. Prouty
*Assistant Examiner*—Richard Hutson
(74) *Attorney, Agent, or Firm*—Darby & Darby

(57) ABSTRACT

The invention relates to *Mycobacterium tuberculosis* RNA polymerase algU sigma subunit protein, DNA encoding, and methods of detecting inhibitors of the RNA polymerase.

4 Claims, 7 Drawing Sheets

OTHER PUBLICATIONS

Schurr, M.J., H. Yu, N. Boucher, and V. Deretic. (1995) Multiple promoters and induction by heat shock of the gen encoding the alternative sigma factor AlgU ($\sigma^E$) which control mucoidy in cystic fibrosis isolates of *Pseudomonus aeruginosa*. J. Bacteriol. 177:5670–5679.

Plorde, J.J., (1994), *Sherris Medical Microbiology*, p 401–415, Ryan, K.J. (ed) Appleton and Lange Press, Norwalk, Ct.

Gross, C.A., Lonetto, M., and Losick, R., (1992) *Transciptional Regulation*, p 129–176, Cold Spring Harbor Laboratory Press, McKnight, S.L. and Yamamoto, K.R. (eds).

von Hippel, P.H., Yager, T.D., Gill, S.C. (1992) p 179–201, *Transciptional Regulation*, Cold Spring Harbor Laboratory Press, McKnight, S.L. and Yamamoto, K.R. (eds).

* cited by examiner

FIG. 3A

```
  1 tctcgatgccaccgcccggtttgggctcttgccgctgcggtgggcgctggcatgcttgctgatcgatatcggcaccgtca 80

 81 cgttttcagcacaacagctgcgcgaactcaccaaaatacgcaatatttgcgcaggccaggtgcggcgcgccggtgg ATG 159
  1                                                                               M   1

160 CTG GCG TAC CGC TTA AAA CGC GGT TGG GCC GTT ATG GTC GAT CCG GGA GTT AGC CCG GGA 219
  2 L   A   Y   R   L   K   R   G   W   A   V   M   V   D   P   G   V   S   P   G    21

220 TGT GTC CGC TTC GTA ACG TTG GAG ATA TCG CCG TCG ATG ACA ATG CAA GGG GAA CGT CTC 279
 22 C   V   R   F   V   T   L   E   I   S   P   S   M   T   M   Q   G   E   R   L    41

280 GAC GCT GTG GTT GCG GAG GCC GTG GCA GGA GAC CGG AAC GCG CTT CGG GAG GTG CTG GAG 339
 42 D   A   V   V   A   E   A   V   A   G   D   R   N   A   L   R   E   V   L   E    61

340 ACC ATC CGC CCG ATC GTC GTG CGA TAT TGC CGA GCG CGA GTC GGC ACG GTC GAG CGG AGC 399
 62 T   I   R   P   I   V   V   R   Y   C   R   A   R   V   G   T   V   E   R   S    81

400 GGC CTG TCA GCA GAT GAC GTG GCA CAG GAG GTG TGC TTG GCC ACC ATA ACG GCG CTG CCG 459
 82 G   L   S   A   D   D   V   A   Q   E   V   C   L   A   T   I   T   A   L   P   101

460 CGC TAT CGG GAC CGC GGC CGG CCA TTC CTG GCG TTT CTG TAC GGC ATC GCG GCG CAC AAG 519
102 R   Y   R   D   R   G   R   P   F   L   A   F   L   Y   G   I   A   A   H   K   121

520 GTT GCC GAC GCC CAT CGG GCA GCC GGC CGT GAC CGG GCC TAT CCC GCC GAA ACG CTT CCT 579
```

```
520 GTT GCC GAC GCC CAT CGG GCA GCC GGC CGT GAC CGG GCC TAT CCC GCC GAA ACG CTT CCT  579
122 V   A   D   A   H   R   A   A   G   R   D   R   A   Y   P   A   E   T   L   P    141

580 GAG CGC TGG TCA GCC GAC GCC GGC CCG GAG CAG ATG GCC ATC GAG GCC GAT TCG GTC ACC  639
142 E   R   W   S   A   D   A   G   P   E   Q   M   A   I   E   A   D   S   V   T    161

640 CGG ATG AAC GAA TTG CTT GAG ATC TTG CCG GCC AAG CAA CGC GAG ATC CTC ATT CTG CGT  699
162 R   M   N   E   L   L   E   I   L   P   A   K   Q   R   E   I   L   I   L   R    181

700 GTT GTC GTC GGC CTG TCC GCG GAA GAG ACC GCC GCC GCC GTC GGC AGC ACC ACG GGG GCG  759
182 V   V   V   G   L   S   A   E   E   T   A   A   A   V   G   S   T   T   G   A    201

760 GTC CGG GTG GCC CAA CAC CGT GCA CTT CAG CGG CTG AAG GAC GAA ATT GTT GCG GCA GGT  819
202 V   R   V   A   Q   H   R   A   L   Q   R   L   K   D   E   I   V   A   A   G    221

820 GAC TAT GCG TGA atttggtaatccccttggcgatcggccgccattggatgagctggcccgcaccgatctgctgctc 895
222 D   Y   A   *                                                                    225

896 gacgcactcgccgaacgggaggaggttgacttcgcggatcctcgcgatgacgcgttggccgccctgctcggacagtggcg 975

976 cgacgacttgaggtggccgccggccagtgccctggtttcacaggacgaggccgtcgccgcgttgcgcgccggggtagcgc 1055

1056 aacggcgacgggctcgtcgcagcctggcggccgtcgggtcggtggccgcg                              1105
```

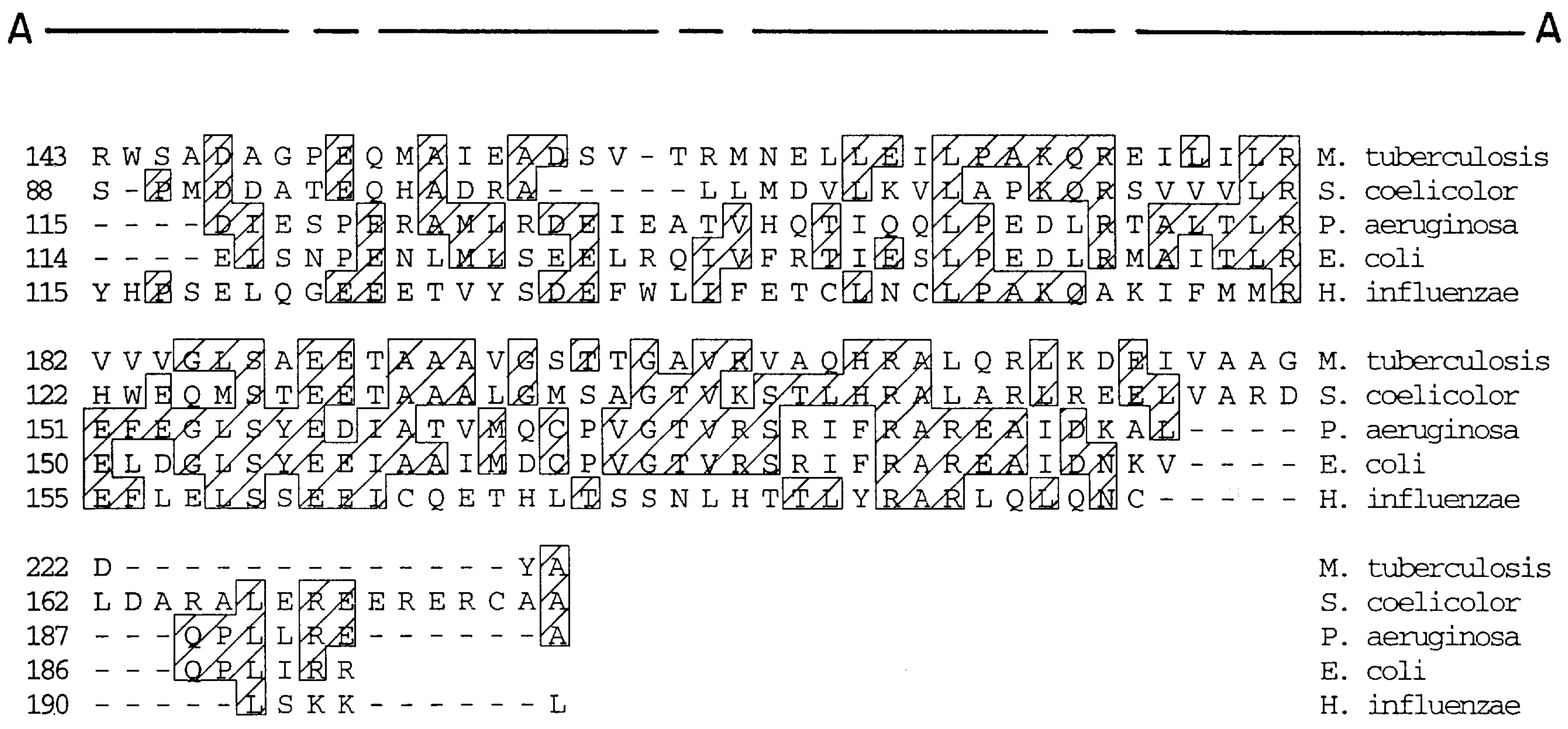

FIG. 4B

```
143 RWSADAGPEQMAIEADSV-TRMNELLEILPAKQREIILIR    M. tuberculosis
 88 S-EMDDATEQHADRA----LLMDVLKVLAPKQRSVVVLR    S. coelicolor
115 ---DIESPRAMLRDEIEATHQIPEDLRTALTLR          P. aeruginosa
114 ---ESNPENLMLSEELRQLVFRTHESLPEDLRMAITLR     E. coli
115 YHESELQGEETVYSDFWLFETCLNCLPAKQAKIFMMR      H. influenzae

182 VVVGLSAEETAAAVGSITGAVRVAQHRALQRELKDEIVAAG  M. tuberculosis
122 HWEQMSTEETAAALGMSAGTVKSTLHRALARLREELVARD   S. coelicolor
151 EFEGLSYEDIATVMQCPVGTVRSRIFRAREAIDKAL----   P. aeruginosa
150 ELDGLSYEEIAAIMDCPVGTYRSRIFRAREAIDNKV----   E. coli
155 EFLELSEEICQETHLLSSNLHTTLYRARLQLQNC-----    H. influenzae

222 D-------YA                                M. tuberculosis
162 LDARALERERERCAA                           S. coelicolor
187 ---OPLLRE----A                            P. aeruginosa
186 ---OPLIRR                                 E. coli
190 ----ISKK------L                           H. influenzae
```

NUCLEIC ACID ENCODING *M. TUBERCULOSIS* ALGU PROTEIN

This application claims priority pursuant to 35 U.S.C. §119 from Provisional Application Ser. No. 60/035,391 filed Jan. 16, 1997, the entire disclosure of which is hereby incorporated by reference.

BACKGROUND OF THE INVENTION

Mycobacteria are gram-positive bacilli, nonmotile rod-shaped organisms that do not form spores. The composition of the cell wall includes a very high concentration of lipids complexed to a variety of peptides and polysaccharides. The unusual structure of the cell wall distinguishes mycobacteria from most other bacteria and is detectable by its resistance to acid-alcohol staining.

The disease caused by *M. tuberculosis* is a progressive, deadly illness that tends to develop slowly and follows a chronic course (Plorde, 1994). It is presently estimated that one-third of the world's population is infected with *M. tuberculosis,* 30 million of whom have active disease (Plorde, 1994). An additional 8 million people develop the disease annually (Plorde, 1994). Most infections are caused by inhalation of droplet nuclei carrying the mycobacterium. A single cough can generate 3000 infected droplet nuclei and even 10 bacilli may be sufficient to cause a pulmonary infection. In addition to the primary infection, reactivation of the disease can occur in older people and in immunocompromised patients.

When intracellular pathogens, such as *Mycobacterium tuberculosis,* are ingested by macrophages the bacteria are under environmental stress. The genes required for survival following uptake by macrophages can provide insight into mycobacterial pathogenesis, and provide novel targets for developing antibacterial agents. The ability to adapt to the intracellular stress requires regulation of complex gene expression and this regulation may be mediated in part by one or more alternative sigma factors. Therefore stress response alternative sigma factors (sigE family) from *M. tuberculosis* are potential novel targets for antibacterial therapeutics.

Extracellular environmental stress can significantly affect the survival of the bacteria. As part of the adaptive response by the bacteria the alternative sigma factors play a critical role in coordinate regulation of gene expression. For example, survival following extreme temperature in *Escherichia coli* is regulated by a family of alternative sigma factors known as the sigE family (Keiichiro et al., Raina et al., Rouviere et al.). Alginate production in *Pseudomonus aeruginosa* is also regulated by the sigE family member known as the algU gene (Deretic et al.). Respiratory infections with mucoid *P. aeruginosa* in cystic fibrosis (CF) patients are the major cause of mortality. Although initial colonizing strains are nonmucoid, the bacteria are converted to mucoid *P. aeruginosa* in the CF lung. This conversion to mucoidy is regulated by the alternative sigma factor algU (Martin et al.).

Sigma (σ) factors are positive regulators of general transcription initiation that enhance transcriptional specificity. The basic unit of the eubacterial transcription apparatus is the DNA-dependent RNA polymerase holoenzyme, a complex consisting of five protein subunits: two copies of the α subunit and one copy each of the β, β', and σ subunits. The α, β and β' subunits are invariant in a given bacterial species and together form core RNA polymerase. Open promoter complexes form only when holoenzyme is bound at a promoter (Gross et al., 1992). When the newly synthesized RNA chain is 8–9 nucleotides long, σ factor dissociates from the complex and the elongation process is begun (von Hippel, et al., 1992). After transcription is terminated, σ factor rebinds core polymerase, creating holoenzyme for another round of initiation (von Hippel, et al., 1992). This series of biochemical activities has been termed "the transcription cycle".

Rifampicin, a highly specific inhibitor of mycobacterium/RNA polymerase, is one of the primary drugs of choice for treatment of tuberculosis. Combination treatment with isoniazid is typical if there is no risk of developing multi-drug resistance. Prolonged treatment regimens are necessary and can take up to nine months. Failure to complete the prolonged treatment course is one of the contributing factors in the development of resistant bacterial strains. Rifabutin is an effective analog of rifampicin, but 70% of rifampicin-resistant strains are also rifabutin-resistant.

Although RNA polymerase is a well-validated target for anti-mycobacterial therapy, discovery of inhibitors of *M. tuberculosis* RNA polymerase is hampered by a lack of information concerning components of the *M. tuberculosis* transcriptional apparatus, difficulties in obtaining sufficient yields of active enzymes for biochemical studies, and technical and biosafety concerns surrounding the handling of live cultures of *M. tuberculosis.* Establishment of an in vitro transcription system employing purified and reconstituted RNA polymerase would greatly advance efforts to identify new therapeutic agents active against tuberculosis. It is very possible that molecules that inhibit a functions may not affect eukaryotic general transcription. Thus, σ factors are a reasonable target for development of transcriptional inhibitors. Therefore, molecules that inhibit σ factor function may be used as general transcriptional inhibitors and antibacterial therapeutics.

Accordingly, there is a need in the art for compositions and methods utilizing cloned genes and purified proteins derived from *M. tuberculosis* RNA polymerase.

SUMMARY OF THE INVENTION

The present invention is based on the isolation and characterization of DNA encoding the σ subunit of RNA polymerase derived from the algU gene from *M. tuberculosis.* In one aspect, the invention provides a purified, isolated nucleic acid having the sequence shown in FIG. 3 SEQ ID NO:1. The invention also encompasses sequence-conservative and function-conservative variants of this sequence. The invention also provides vectors comprising these sequences, and cells comprising the vectors.

In another aspect, the present invention provides a purified, isolated polypeptide encoded by the nucleic acid sequence shown in FIG. 3, as well as function-conservative variants thereof.

In yet another aspect, the invention provides in vitro methods for high-throughput screening to detect inhibitors of *M. tuberculosis* RNA polymerase. The methods are carried out by the steps of:

a) providing a mixture comprising
   (i) purified *M. tuberculosis* RNA polymerase containing the algU σ factor and
   (ii) a DNA template encoding a promoter sequence that is recognized by *M. tuberculosis* RNA polymerase containing the algU subunit;
b) incubating the mixture in the presence of test compounds to form test samples, and in the absence of test compounds to form control samples, under conditions that result in RNA synthesis in the control samples;

c) measuring RNA synthesis in the test and control samples; and d) comparing the RNA synthesis detected in step (c) between the test and control samples. According to the invention, an RNA polymerase inhibitor is a test compound that causes a reduction in RNA synthesis measured in the test sample relative to RNA synthesis measured in the control sample.

In yet another aspect, the invention provides in vivo methods for high-throughput screening to detect inhibitors of *M. tuberculosis* RNA polymerase. The methods are carried out by the steps of:

a) providing a non-mycobacterial bacterial strain, preferably *E. coli,* that (i) has been transformed with a DNA template encoding a promoter sequence that is recognized by *M. tuberculosis* RNA polymerase containing the algU subunit, and (ii) expresses enzymatically active *M. tuberculosis* RNA polymerase (e.g., α, β, β' plus the algU σ subunit disclosed herein);

b) incubating the bacterial strain of (a) in the presence of test compounds to form test samples, and in the absence of test compounds to form control samples;

c) measuring RNA synthesis in the test and control samples; and d) comparing the RNA synthesis detected in step (c) between the test and control samples. According to the invention, an RNA polymerase inhibitor is a test compound that causes a reduction in RNA synthesis measured in the test sample relative to RNA synthesis measured in the control sample.

These and other aspects of the present invention will be apparent to those of ordinary skill in the art in light of the present specification and appended claims.

DESCRIPTION OF THE DRAWINGS

FIG. 3. Nucleotide and deduced amino acid sequences of the *M. tuberculosis* H37Rv algU gene SEQ ID NO:1 and SEQ ID NO:2, respectively.

DETAILED DISCUSSION OF THE INVENTION

All patents, patent applications and literature references cited herein are hereby incorporated in their entirety. In the case of inconsistencies, the present disclosure will prevail.

Figure 1:
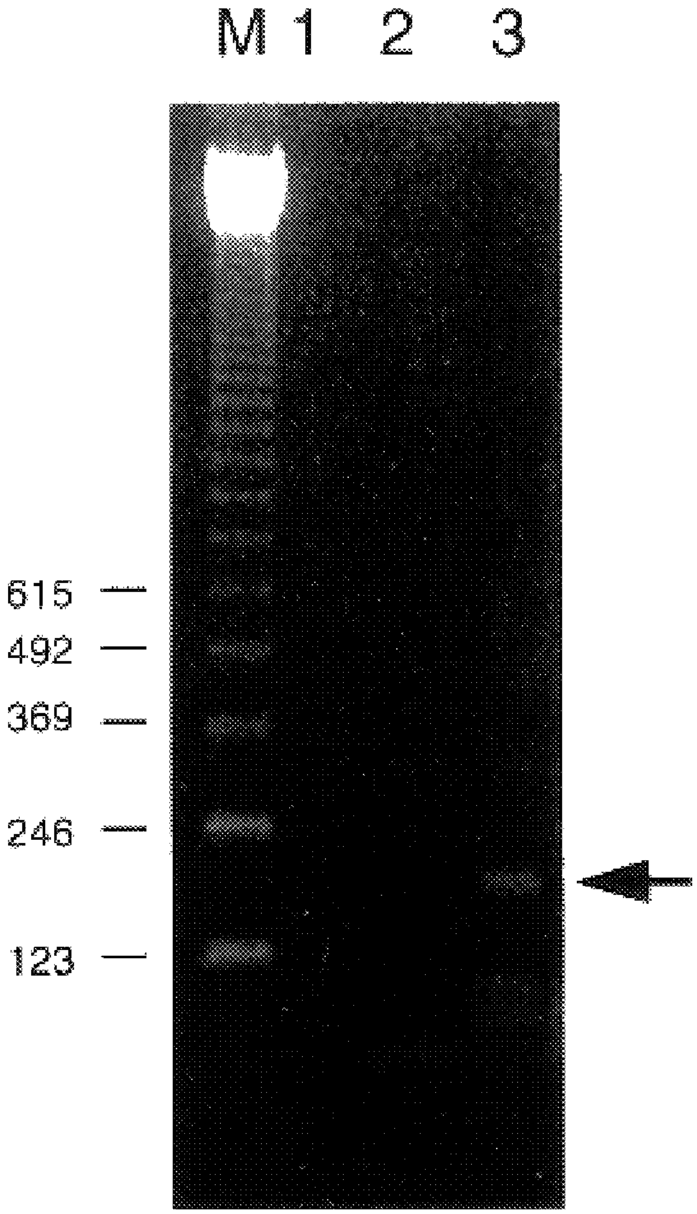
FIG. 1. PCR amplification of *M. tuberculosis* H37Rv genomic DNA. lane M: DNA marker (123 bp, Gibco-BRL), lane 1: primer P1 only, lane 2: primer P2 only, lane 2: primer P2 only and lane 3: primer P1 and P2. The amplified DNA fragment (arrow in FIG. 1) was gel purified and subcloned into pCRScript (Stratagene) plasmid.
Figure 2A:
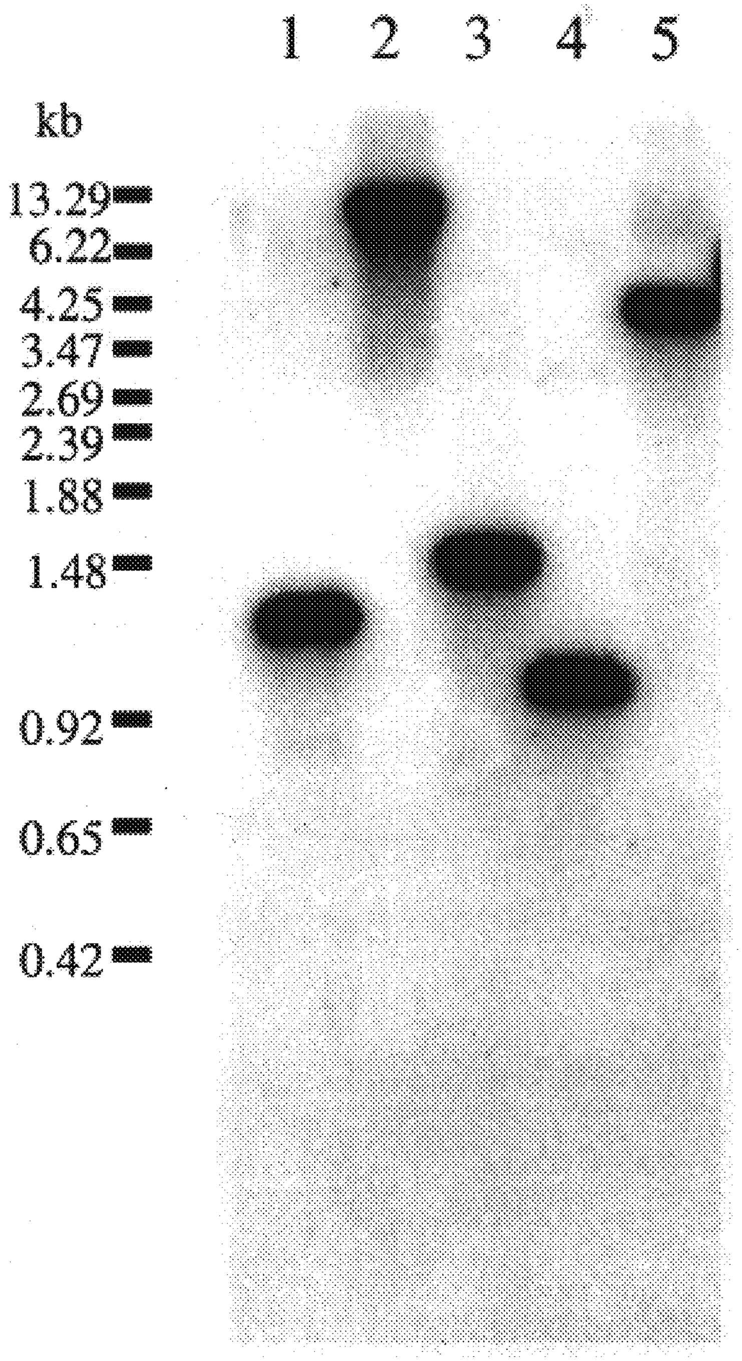
FIG. 2A. Southern blot analysis of *M. tuberculosis* H37Rv DNA and cosmid clones. A. *M. tuberculosis* H37Rv genomic DNA were digested with restriction enzymes: BamH I (lane 1), Pst I (lane 2), Pvu II (lane 3), Sma I (lane 4) and Xmn I (lane5) and analyzed by Southern hybridization using the PCR amplified DNA fragment as a probe. Sizes of DNA markers ($^{35}$S-DNA Marker, Amersham) are indicated in kb. 2B. Two different positive clones (designated 2D11 and 4D11) isolated from an *M. tuberculosis* cosmid library were digested with BamH I (lane 1 and 4), Pvu II (lane 2 and 5) and Sma I (lane 3 and 6) and hybridized with the PCR-generated sigma gene as a probe.
Figure 4A:
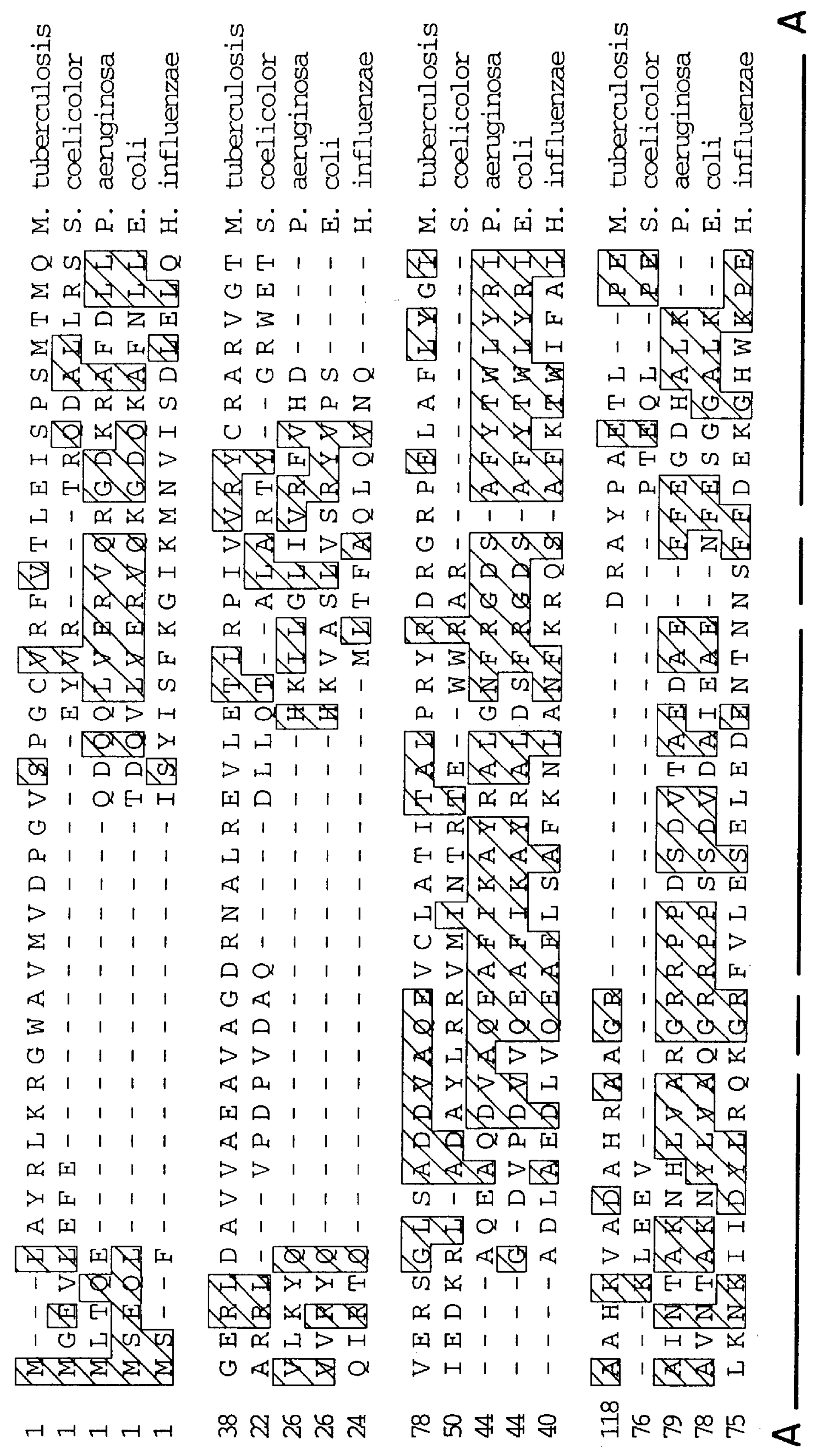
FIG. 4. Alignment of the inferred amino acid sequence of the *M. tuberculosis* (Mt) H37Rv algU gene with sequences of extracellular function family of sigma subunits from other bacteria (*Streptomyces coelicolor* SEQ ID NO:3, *Pseudomonas aeruginosa* SEQ ID NO:4, *Escherechia coli* SEQ ID NO:5 and *Hemophilus influenzae* SEQ ID NO:6) Shading indicates identical amino acid residues. Amino acid sequence alignments were performed using MegAlign (DNAStar).

The present invention is based on the isolation of a fragment of the *M. tuberculosis* algU gene, encoding an alternative σ subunit of RNA polymerase. As described in Example 1 below. PCR amplification of *M. tuberculosis* genomic DNA with primers based on the *M. leprae* algU DNA sequence generated an expected size of DNA (180 base pairs) (FIG. 1). The PCR amplified DNA had >90% identity to the *M. leprae* gene. Southern blot analysis demonstrated the presence of a single copy of this gene in *M. tuberculosis* (FIG. 2A). The amplified DNA was utilized as a hybridization probe to recover the entire algU gene from a cosmid library of genomic DNA from virulent *M. tuberculosis* strain H37RV. Nucleotide sequencing indicated that the 675 bp *M. tuberculosis* algU open reading frame (ORF) encodes a protein of 24.3 kDa (225 amino acids) which shows significant structural similarity to the σ subunits of diverse bacterial species with greatest identity to the stress related extracellular function family of σ subunits of *Streptomyces coelicolor, Pseudomonas aeruginosa, Escherochia coli* and *Hemophius influenzae.* The sigma factors from *S. coelicolor* SEQ ID NO:3 and *P. aeruginosa* , SEQ ID NO4, *E. coli* and *H. influenzae* SEQ ID NO:6 are 24%, 20%, 21% and 16% identical to the *M. tuberculosis* sequence SEQ ID NO:5 respectively (FIG. 4).

The *P. aeruginosa* algU gene is part of a large operon that contains genes for anti-sigma factors (mucA and mucB) and a protease (mucD) (Schurr et al.). Further nucletodide sequencing and availability of an integrated map of the genome of *M. tuberculosis* H37Rv (Philipp et al., 1996) is expected to clarify the structural organization and position of the algU locus of *M. tuberculosis.*

In practicing the present invention, many techniques in molecular biology, microbiology, recombinant DNA, and protein biochemistry such as these explained fully in, for example, Sambrook et al., 1989, *Molecular Cloning: A Laboratory Manual,* Second Edition, Cold Spring Harbor Laboratory Press, Cold Spring Harbor, N.Y.; *DNA Cloning: A Practical Approach,* Volumes I and II, 1985 (D.N. Glover ed.); *Oligonucleotide Synthesis,* 1984, (M. L. Gait ed.); *Transcription and Translation,* 1984 (Hames and Higgins eds.); A Practical Guide to Molecular Cloning; the series, *Methods in Enzymology* (Academic Press, Inc.); and *Protein Purification: Principles and Practice,* Second Edition (Springer-Verlag, N.Y.), may be used.

The present invention encompasses nucleic acid sequences encoding the algU gene of *M. tuberculosis,* enzymatically active fragments derived therefrom, and related sequences. As used herein, a nucleic acid that is "derived from" a sequence refers to a nucleic acid sequence that corresponds to a region of the sequence, sequences that are homologous or complementary to the sequence, and "sequence-conservative variants" and "function-conservative variants". Sequence-conservative variants are those in which a change of one or more nucleotides in a given codon position results in no alteration in the amino acid encoded at that position. Function-conservative variants are those in which a given amino acid residue in the algU subunit has been changed without altering the overall conformation and function of the polypeptide, including, but not limited to, replacement of an amino acid with one having similar physico-chemical properties (such as, for example, acidic, basic, hydrophobic, and the like). Fragments of the algU subunit that retain enzymatic activity can be identified according to the methods described herein, e.g., expression in *E. coli* followed by enzymatic assay of the cell extract.

The nucleic acids of the present invention include purine- and pyrimidine-containing polymers of any length, either polyribonucleotides or polydeoxyribonucleotides or mixed polyribo-polydeoxyribo nucleotides. This includes single- and double-stranded molecules, i.e., DNA-DNA, DNA-RNA and RNA-RNA hybrids, as well as “protein nucleic acids” (PNA) formed by conjugating bases to an amino acid backbone. This also includes nucleic acids containing modified bases. The nucleic acids may be isolated directly from cells. Alternatively, PCR can be used to produce the nucleic acids of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression.

The nucleic acids of the present invention may be flanked by natural *M. tuberculosis* regulatory sequences, or may be associated with heterologous sequences, including promoters, enhancers, response elements, signal sequences, polyadenylation sequences, introns, 5'- and 3'-noncoding regions, and the like. The nucleic acids may also be modified by many means known in the art. Non-limiting examples of such modifications include methylation, “caps”, substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The nucleic acid may be derivatized by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

The invention also provides nucleic acid vectors comprising the disclosed algU subunit sequences or derivatives or fragments thereof. A large number of vectors, including plasmid and fungal vectors, have been described for replication and/or expression in a variety of eukaryotic and prokaryotic hosts. Non-limiting examples include pKK plasmids (Clontech), pUC plasmids, pET plasmids (Novagen, Inc., Madison, Wis.), or pRSET or pREP (Invitrogen, San Diego, Calif.), and many appropriate host cells, using methods disclosed or cited herein or otherwise known to those skilled in the relevant art. Recombinant cloning vectors will often include one or more replication systems for cloning or expression, one or more markers for selection in the host, e.g. antibiotic resistance, and one or more expression cassettes. Suitable host cells may be transformed/transfected/infected as appropriate by any suitable method including electroporation, $CaCl_2$ mediated DNA uptake, fungal infection, microinjection, microprojectile, or other established methods.

Appropriate host cells include bacteria, archebacteria, fungi, especially yeast, and plant and animal cells, especially mammalian cells. Of particular interest are *E. coli, B. subtilis, Saccharomyces cerevisiae, Saccharomyces carlsbergensis, Schizosaccharomyces pombe,* SF9 cells, C129 cells, 293 cells, Neurospora, and CHO cells, COS cells, HeLa cells, and immortalized mammalian myeloid and lymphoid cell lines. Preferred replication systems include M13, ColE1, SV40, baculovirus, lambda, adenovirus, and the like. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced Mycobacterial-derived peptides and polypeptides.

Advantageously, vectors may also include a transcription regulatory element (i.e., a promoter) operably linked to the algU subunit portion. The promoter may optionally contain operator portions and/or ribosome binding sites. Non-limiting examples of bacterial promoters compatible with *E. coli* include: trc promoter, β-lactamase (penicillinase) promoter; lactose promoter; tryptophan (trp) promoter; arabinose BAD operon promoter; lambda-derived P1 promoter and N gene ribosome binding site; and the hybrid tac promoter derived from sequences of the trp and lac UV5 promoters. Non-limiting examples of yeast promoters include 3-phosphoglycerate kinase promoter, glyceraldehyde-3-phosphate dehydrogenase (GAPDH) promoter, galactokinase (GALI) promoter, galactoepimerase promoter, and alcohol dehydrogenase (ADH) promoter. Suitable promoters for mammalian cells include without limitation viral promoters such as that from Simian Virus 40 (SV40), Rous sarcoma virus (RSV), adenovirus (ADV), and bovine papilloma virus (BPV). Mammalian cells may also require terminator sequences and poly A addition sequences, and enhancer sequences which increase expression may also be included. Sequences which cause amplification of the gene may also be desirable. Furthermore, sequences that facilitate secretion of the recombinant product from cells, including, but not limited to, bacteria, yeast, and animal cells, such as secretory signal sequences and/or prohormone pro region sequences, may also be included.

Nucleic acids encoding wild-type or variant subunit polypeptides may also be introduced into cells by recombination events. For example, such a sequence can be introduced into a cell, and thereby effect homologous recombination at the site of an endogenous gene or a sequence with substantial identity to the gene. Other recombination-based methods, such as non-homologous recombinations or deletion of endogenous genes by homologous recombination, may also be used.

algU subunit-derived polypeptides according to the present invention, including function-conservative variants, may be isolated from wild-type or mutant *M. tuberculosis* cells, or from heterologous organisms or cells (including, but not limited to, bacteria, fungi, insect, plant, and mammalian cells) into which a subunit-derived protein-coding sequence has been introduced and expressed. Furthermore, the polypeptides may be part of recombinant fusion proteins. Alternatively, polypeptides may be chemically synthesized by commercially available automated procedures, including, without limitation, exclusive solid phase synthesis, partial solid phase methods, fragment condensation or classical solution synthesis.

“Purification ” of a σ subunit polypeptide refers to the isolation of the polypeptide in a form that allows its enzymatic activity to be measured without interference by other components of the cell in which the polypeptide is expressed. Methods for polypeptide purification are well-known in the art, including, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against the σ subunit or against peptides derived therefrom can be used as purification reagents. Other purification methods are possible.

The isolated polypeptides may be modified by, for example, phosphorylation, sulfation, acylation, or other protein modifications. They may also be modified with a label capable of providing a detectable signal, either directly or indirectly, including, but not limited to, radioisotopes and fluorescent compounds.

Screening Methods to Identify Anti-tuberculosis Agents

The methods and compositions of the present invention can be used to identify compounds that inhibit the function of *M. tuberculosis* RNA polymerase and thus are useful as anti-tuberculosis agents. This is achieved by providing active recombinant algU subunit according to the present invention, in combination with other components of RNA polymerase, in a context in which the inhibitory effects of test compounds can be measured.

In a preferred embodiment, recombinant *M. tuberculosis* RNA polymerase subunits (α, β, β' plus the σ subunit disclosed herein) are purified in milligram quantities from *E. coli* cultures by affinity methods utilizing a hexahistidine tagged α and σ subunits. Enzymatically active holoenzyme is reconstituted using these components. The active polymerase is then incubated in the presence of test compounds to form test mixtures, and in the absence of test compounds to form control mixtures. In vitro transcription is then carried out using a DNA template containing appropriate promoter and reporter sequences. (See Example 3 below.)

In another embodiment, *M. tuberculosis* RNA polymerase subunits (α, β, β' plus the σ subunit disclosed herein) are co-expressed in *E. coli* or another surrogate bacterial cell, in conjunction with an appropriate promoter-reporter gene. The ability of test compounds to differentially inhibit *M. tuberculosis* RNA polymerase is then assessed.

*M. tuberculosis* promoters useful in practicing the invention include without limitation: hsp 60 promoter (Stover et al., 1991); cpn-60 promoter (Kong et al., 1993); 85A antigen promoter (Kremer, 1995); PAN promoter (Murray et al., 1992); 16S RNA promoter (Ji et al., 1994); and asks promoter (Cirillo et al., 1994). Useful reporter genes include without limitation xy1E (Curcic et al., 1994); CAT (Das Gupta et al., 1993); luciferase (Cooksey et al., 1993); green fluorescent protein (Dhadayuthap et al., 1995); and lacZ (Silhavy et al., 1985).

It will be understood that the present invention encompasses *M. tuberculosis* RNA polymerases containing the algU σ factor disclosed herein, which is used in conjunction with particular promoters that are recognized by RNA polymerase containing this σ factor. The invention also encompasses the identification of additional promoters that are recognized by the particular σ subunit of the present invention. This is achieved by providing a library of random *M. tuberculosis* gene fragments cloned upstream of an appropriate reporter gene (see above). The library is transformed into *M. tuberculosis* or *M. smegmatis* and reporter gene expression is measured. Alternatively, the library is transformed into another bacterial cell, such as, e.g., *E. coli,* which expresses *M. tuberculosis* RNA polymerase core subunits as well as the σ subunit of the present invention and cognate promoters that drive reporter gene expression. In yet another embodiment, expression of an *M. tuberculosis* σ factor confers new recognition properties on *E. coli* RNA polymerase and permits isolation of promoters utilized specifically by a particular *M. tuberculosis* σ subunit.

Preferably, both in vitro and in vivo screening methods of the present invention are adapted to a high-throughput format, allowing a multiplicity of compounds to be tested in a single assay. Such inhibitory compounds may be found in, for example, natural product libraries, fermentation libraries (encompassing plants and microorganisms), combinatorial libraries, compound files, and synthetic compound libraries. For example, synthetic compound libraries are commercially available from Maybridge Chemical Co. (Trevillet, Cornwall, UK), Comgenex (Princeton, N.J.), Brandon Associates (Merrimack, N.H), and Microsource (New Milford, Conn.). A rare chemical library is available from Aldrich Chemical Company, Inc. (Milwaukee, Wis.). Alternatively, libraries of natural compounds in the form of bacterial, fungal, plant and animal extracts are available from, for example, Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., *TibTech* 14:60, 1996). preferably using automated equipment, to allow for the simultaneous screening of a multiplicity of test compounds.

Useful anti-tuberculosis compounds are identified as those test compounds that decrease tuberculosis-specific transcription. Once a compound has been identified by the methods of the present invention as an RNA polymerase inhibitor, in vivo and in vitro tests may be performed to further characterize the nature and mechanism of the inhibitory activity. For example, classical enzyme kinetic plots can be used to distinguish, e.g., competitive and non-competitive inhibitors.

Compounds identified as RNA polymerase inhibitors using the methods of the present invention may be modified to enhance potency, efficacy, uptake, stability, and suitability for use in pharmaceutical formulations, etc. These modifications are achieved and tested using methods well-known in the art.

The present invention is further described in the following examples which are intended to further describe the invention without limiting the scope thereof.

EXAMPLE 1

In the present Example, the following Materials and Methods were used.

PCR amplification: Based on the *M. leprae* cosmid sequence (cosmid B-1620, Genbank accession #U-00015, position 36121-35942), a set of primers was designed and the sequence of these primers was: 5'-ATGAACGAACTGCTCGAGATCTTGCCTGCC-3' (P1) SEQ ID NO:7 and 5'-TCACCCGCCGCGACGATCTCGGACGTCAAC-3' (P2) SEQ ID NO:8. Amplification was performed using 100 ng of *M. tuberculosis* H37Rv genomic DNA using a programmable thermal controller (PTC100, M J Research, Inc.). The PCR conditions were as follows: reaction volume 100 μl; pfu cloned DNA polymerase (Stratagene); 0.2 mM dNTPs (Boehringer-Mannheim); 100 ng of primer; one cycle of 94° C. for 1 minute, thirty cycle of 94° C. for one minute, 50° C. for one minute and 72° C. for one minute.

Southern blot analysis: Restriction enzyme digests of *M. tuberculosis* H37Rv chromosomal DNAs were electrophoresed on 1% TAE-agarose gels and transferred to nytran membranes (Schleicher and Schuell) using a Pressure Blotter (Stratagene). Probe labeling was performed using the rediprime DNA labelling system (Amersham) essentially as described by the supplier. Hybridization was performed using 6×SSC, 5×Denhardt solution, 0.5% SDS, 0.1 mg per ml Salmon Sperm DNA and 50% formamide. Washing was performed using 2×SSC, 0.5%SDS, at room temperature for 15 min and 0.1×SSC, 0.5% SDS at 37° C. for 15 min.

Cosmid hybridizations: A transducing lysate of a cosmid library of *M. tuberculosis* H37Rv genomic DNA in vector pYA3060 was generously supplied by Dr. J. Clark-Curtiss. Cosmid-bearing *E. coli* $\chi$2819T (Jacobs et al, 1986) colonies representing roughly five genomic equivalents were individually picked to wells of sterile 96-well microtiter dishes and propagated at 30° C. in Luria broth containing ampicillin at 30 $\mu$g/ml and thymidine at 50 $\mu$g/ml. Colonies were grown overnight at room temperature on the above media as nylon filter replicas of the library. Filters were processed for colony hybridization by standard methods and probe hybridizations performed as described above. Cosmid DNAs were purified using maxiprep columns (Qiagen).

DNA sequencing and analysis: Plasmid templates for nucleotide sequencing were purified using maxiprep columns (Qiagen). PCR cycle sequencing (ABI Prizm) was carried out with an Applied Biosystems automated sequencer at the Massachusetts General Hospital DNA Sequencing Core Facility, Department of Molecular Biology (Boston, Mass.).

(a) Cloning of *M. tuberculosis* algU Gene

A DNA fragment (180base pair) that contains the *M. tuberculosis* algU gene was identified by using PCR amplification of *M. tuberculosis* H37Rv genomic DNA with primers that were derived from the *M. leprae* cosmid sequence. To determined whether the amplified DNA fragment contains the algU gene, the 180 base pair DNA fragment was subcloned into a pCRScript (Stratagene) plasmid and nucleotide sequences were determined. The deduced amino acid sequence of the PCR product showed significant homology to the algU sequence from other bacteria (FIG. 4).

Figure 2B:
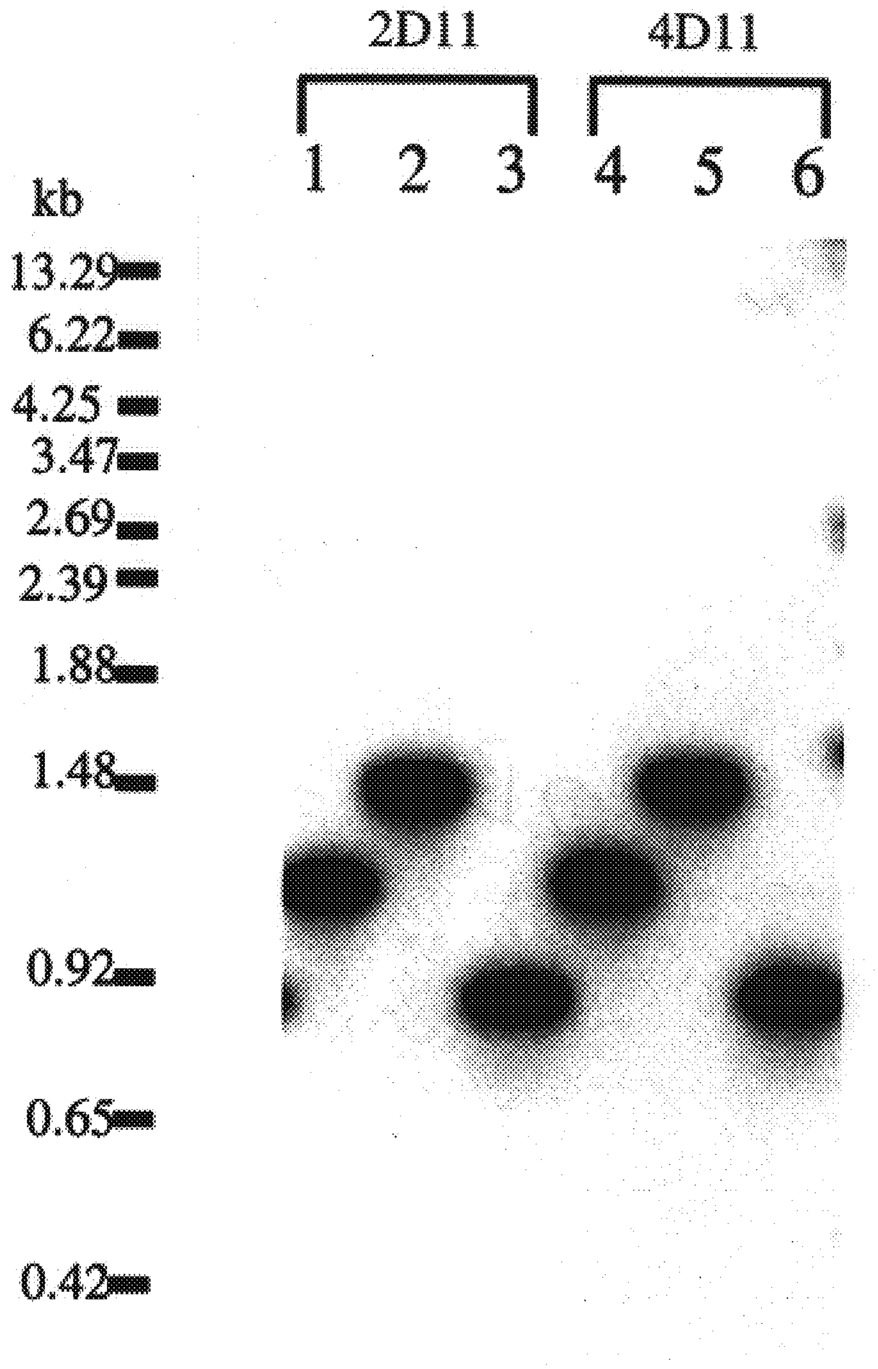

(b) Southern Blot Analysis and Isolation of the Full Length *M. tuberculosis* algU Gene To see whether the cloned algU gene is a single copy of gene in *M. tuberculosis* Southern blot analysis was performed. The PCR cloned DNA fragment was used as a probe to analyzed the *M. tuberculosis* H37Rv genomic DNA that was digested with endonucleases. The PCR cloned DNA probe recognized a single band in each digested chromosomal DNA (FIG. 2), and it was concluded that the algU gene is a single copy of gene in *M. tuberculosis.*

The full-length algU gene was obtained from a cosmid library of *M. tuberculosis* H37Rv genomic fragments (kindly provided by Dr. J. Clark-Curtiss) using the 180 bp as a probe. Screening of 552 cosmid-bearing *E. coli* colonies (representing roughly 5 genome equivalents) with the algU gene fragment yielded 5 positive clones. One algU-hybridizing cosmid clone, 4D11 was analyzed, and Southern blotting of 4D11 DNA digested with a panel of restriction enzymes confirmed that the no gross structural rearrangements of the algU gene had occurred during cloning (FIG. 3) SEQ ID NO:1. The 1.1 kb BamH I, 1.2 kb PvuII and 1 kb Sma I algU-hybridizing fragments of cosmid 4D11 were subcloned into vector pSKII+ prior to nucleotide sequencing.

(c) Sequence Analysis of the *M. tuberculosis* algU Gene

Nucleotide sequencing was performed on plasmid subclones shown in FIG. 4. The sequence encodes a 675 bp ORF which has an overall G+C composition of 63% (85% for bases occupying the codon third position). Assuming that the ATG at position 53–5 serves as the initiator codon, the ORF is expected to encode a protein of 225 amino acids. A strong match with the consensus sequence for an *M. tuberculosis* ribosome binding site (CAGGTG), (Novick, 1996) is positioned just upstream of the putative ATG codon. Examination of more than 63 bp of nucleotide sequence upstream of the translation start site did not reveal regions of exact identity with prokaryotic promoter sites. Among $\sigma$ subunits studied in other bacterial species, the deduced amino acid sequence of the 225 residue *M. tuberculosis* protein displayed greatest similarity to the stress related extracellular function family of sigma subunits of *Streptomyces coelicolor, Pseudomonas aeruginosa, Escherechia coli* and *Hemophilus influenzae* (FIG. 4) SEQ ID NOS:3,4,5, and 6, respectively.

EXAMPLE 2

Others have shown that overexpressed *E. coli* RNA polymerase subunits can be reconstituted into an enzymatically active protein (Zalenskaya et al., 1990; Kashlev et al., 1993; Tang et al., 1995). The *M. tuberculosis* rpoA (Healy et al.), rpoB and rpoC genes (Miller et al., 1994) have been cloned and characterized. Using the overexpressed *M. tuberculosis* RNA polymerase subunits, the in vitro reconstitution assay to form the enzymatically active core enzyme will be performed. Holoenzyme that contains algU sigma subunit can be obtained and biochemical analysis of gene regulation in *M. tuberculosis* will be studied. Transcription inhibitors that act against the holoenzyme that contains the stress related sigma factor will be identified.

EXAMPLE 3

High Throughput Screens for Inhibitors of *M. tuberculosis* RNA Polymerase and $\sigma$ Subunit High-throughput screens for anti-tuberculosis agents may be performed using either an in vitro or in vivo format. In either case, the ability of test compounds to inhibit *M. tuberculosis* RNA polymerase-driven transcription of *M. tuberculosis* promoters is tested.

The algU sigma factor of the present invention regulates transcription of promoters characterized by the sigma promotor consensus sequence: GAACTT-(N16/17)-TCTgA-N (1–5)SEQ ID NO:9 (Deretic, et al., 1994; Erickson, et al., 1989; Lipnska, et al., 1988; Martin, et al., 1994; Scharr, et al., 1995). Therefore, this promoter is preferred for use herein.

a) In vitro screens:

The following procedure is used for cell-free high-throughput screening. A Tomtec Quadra 96-well pipetting station is used to add the reaction components to polypropylene 96-well dishes. 5 $\mu$l aliquots of test compounds dissolved in DMSO (or DMSO alone as a control) are added to wells. This is followed by 20 $\mu$l of the RNA polymerase mixture, which consists of: 10 mM DTT, 200 mM KCl, 10 mM $Mg^{+2}$, 1.5 $\mu$M bovine serum albumin, and 0.25 $\mu$g reconstituted RNA polymerase. After allowing the test compound to interact with the RNA polymerase, 25 $\mu$l of the DNA/NTP mixture is added, containing: 1 $\mu$g template DNA (see above), 4 $\mu$M [$\alpha$-$^{32}$P]-UTP, and 400 $\mu$M each CTP, ATP, and GTP.

After incubation for 30 min at 25° C., the reaction is stopped by addition of 150 μl 10% trichloroacetic acid (TCA). After incubation at room temperature for 60 min, the TCA-precipitated RNA is adsorbed onto double-thick glass fiber filtermats using a Tomtec cell harvester. The wells of the microtiter plate and the filter are washed twice with 5% TCA and bound radioactivity is determined using a Wallac microbeta 1450 scintillation counter.

Inhibitory activity due to the test compound is calculated according to the formula:

$$\% \text{ inhibition} = \frac{(cpm_{\text{positive control}} - cpm_{\text{sample}})}{cpm_{\text{positive control}}} \times 100$$

where $cpm_{positive\ control}$ represents the average of the cpm in wells that received DMSO alone, and $cpm_{sample}$ represents the cpm in the well that received test compound. Compounds that cause at least 50% inhibition are scored as positive "hits" in this assay.

As an additional control, rifampicin is used at a concentration of 30 nM, which results in a 50–75% inhibition of transcription in this assay.

b) In vivo screen:

*M. tuberculosis* RNA polymerase subunits (α, β, β', and the σ subunit disclosed herein) are expressed in *E. coli* under the control of regulatable promoters by transforming *E. coli* with appropriate plasmids. If the σ subunit is expressed, a DNA sequence comprising the sigE promoter described above is also introduced into the cells to serve as a template for *M. tuberculosis*-specific transcription.

In one embodiment, the sigE promoter sequence is linked to a DNA sequence encoding the xylE gene product, catechol 2, 3-dioxygenase (CDO). When expressed in the *E. coli* cell, CDO converts catechol to 2-hydroxymuconic semialdehyde, which has a bright yellow color (having an absorbance maximum at 375 nm) that is easily detected in whole cells or in crude extracts. The substrate for this enzyme is a small aromatic molecule that easily enters the bacterial cytoplasm and does not adversely affect cell viability.

In a high-throughput format, aliquots of bacterial cultures are incubated in the absence or presence of test compounds, and CDO activity is monitored by measuring absorbance at 375 nm following addition of catechol.

c) Specificity:

Compounds that score as positive in either the in vitro or in vivo assays described above are then tested for their effect on human RNA polymerase II. Those compounds which do not significantly inhibit human RNA polymerase II will be further developed as potential anti-tuberculosis agents.

REFERENCES

Cirillo et al. (1994) *Mol.Microbiol.* 11:629.

Cooksey et al. (1993) *Antimicrob.Agents.Chemother.* 37:1348.

Curcic et al. (1994) *Mol.Microbiol.* 13:1057.

Das Gupta et al. (1993) *J.Bacteriol.* 175:5186.

Dhadayuthap et al. (1995) *Mol.Microbiol.* 17:901.

Jacobs, W. R., et al., (1986) "In vivo repackaging of recombinant cosmid molecules for analyses of *Salmonella typhimurium, Streptococcus mutants,* and Mycobacterial Genomic libraries". *Infect. Immun.* 52:101–109.

Ji et al. (1994) *Microbiol.* 140:2829.

Kong, et al. (1993) Proc.Natl.Acad,Sci.USA 90:2608.

Kremer (1995) *J. Bacteriol.* 177:642.

Malakooti et al. (199 ) *J.Bacteriol.* 177:6854.

Murray et al. (1992) *Mol. MicrObiol.* 6:3331.

Novick, R. (1996) "Mycobacteria: Growth, Metabolism, and Molecular Biology". *Tuberculosis* (Little, Brown, and Co., Boston, Mass.) pp 187–198.

Stover et al., (1991) *Nature* 351:456

Silhavy et al. (1985) *Microbiol.Rev.* 49:398.

Tang, H., et al., (1995) "Rapid RNA polymerase genetics: One-day, no-column preparation of reconstituted recombinant *Escherichia coli* RNA polymerase". *Proc. Natl. Acad. Sci. USA* 92:4902–4906.

Weiden, M. et al., (1996) "*Genetics of M. tuberculosis*". In Tuberculosis (Little, Brown, and Co., Boston, Mass.) pp 211–222.

Yura and Ishihama (1979) Genetics of bacterial RNA polymerases. *Ann. Rev. Genet.* 13:59–97.

Vall-Spinosa, A. et al., *N. Engl. J. Med.* 283:616–621, 1970

Zalenskaya, K. et al., *Gene* 89:7–12.

Deretic, V., M. Schurr, J. Boucher, and D. Martin. (1994) Conversion *Pseudomonus aeruginosa* mucoidy in cystic fibrosis: environmental stress and regulation of bacterial virulence by alternative sigma factors. *J Bacteriol* 17: 2773–2780.

Healy, J. H., J. Bodorova, K. Lam, C. Wobbe (1996) The rpoA gene of *Mycobacterium tuberculosis.* Submitted for publication.

Kashlev, M., Martin, E., Polyakov, A., Severinov, K., Nikiforov, V., and Goldfarb, A. (1993) Histidine-tagged RNA polymerase: dissection of the transcription cycle using immobilized enzyme. Gene 130: 9–14.

Keiichiro, H., M. Amemura, H. Nashimoto, H. Shinagawa, and S. Makino. (1995) The rpoE gene of *Escherichia coli,* which encodes $\sigma^E$, is essential for bacterial growth at high temperature. *J Bacteriol* 177:2918–2922.

Martin, D., M. Scurr, M. Mudd, J. Govan, B. Holloway, and V. Deretic (1993) *Proc. Natl. Acad. Sci.* 90: 8377–8381.

Miller, L., Crawford, J. T., and Shinnick, T. M. (1994) The rpoB gene of *Mycobacterium tuberculosis.* Antimicrob. Agents. Chemo. 38: 805–811.

Philipp, W. J., Poulet, S., Eiglmeier, K., Pascopella, L., Balasubramanian, V., Heym, B., Bergh, S., Bloom, B. R., Jacobs, W. R., and Cole, S. T. (1996) Proc. Natl. Acad. Sci. USA 93: 3132–3137.

Raina, S., D.Missiakas, and C. Geogopoulos. (1995) The rpoE encoding the $\sigma^E(\sigma^{24})$ heat shock sigma factor of *Escherichia coli. EMBO J* 14: 1043–1055.

Rouviere, P., A. De Las Penas, C. Lu, K. Rudd, and C. Gross. (1995) rpoE the gene encoding the second heat-shock sigma factor, $\sigma^E$, in *Escherichia coli. EMBO J* 14: 1032–1042.

Schurr, M. J., H. Yu., J. M. Martinez-salazar, J. C. Boucher and V. Deretic. (1996) Control of algU, a member of the $\sigma^E$-like family of stress sigma factors, by the negative regulators mucA and mucB and *Pseudomonas aeruginosa* conversion to mucoidy in cystic fibrosis. *J. Bacteriol* 178:4997–5004.

Tang, H., Severinov, K., Goldfarb, A., and Ebright, R. H. (1995) Rapid RNA polymerase genetics: One-day, no-column preparation of reconstituted recombinant *Escherichia coli* RNA polymerase. Proc. Natl. Acad. Sci. USA 92: 4902–4906.

Zalenskaya, K., Lee, J., Gujuluva, C. N., Shin, Y. K., Slutsky, M. and Goldfarb, A. (1990) recombinant RNA polymerase: inducible overexpression, purification, and assembly of *Escherichia coli* rpo gene products. Gene 89: 7–12.

Deretic, V., M. Schurr, J. Boucher, and D. Martin. (1994) Conversion *Pseudomonus aeruginosa* mucoidy in cystic fibrosis: environmental stress and regulation of bacterial virulence by alternative sigma factors. J Bacteriol. 17:2773–2780.

Erickson, J. W., and C. A. Gross. (1989) Identification of the sigma subunit of *Escherichia coli* polymerase: a second sigma factor involved in high-temperature gene expression. Genes Dev. 3:1462–1471.

Lipnska, B., S. Sharma, and C. Georgopoulos. (1988) Sequence analysis and regulation of the htra gene of *Escherichia coli:* a $\sigma^{32}$-independent mechanism of heat-inducible transcription. Nucleic Acids Res. 16:10053–10067.

Martin, D. W., M. J. Schurr, H. Yu, and V. Deretic. (1994) Analysis of promoters controlled by the putative sigma factor AlgU regulating conversion to mucoidy in *Pseudomonas aeruginosa:* relationship to stress response. J. Bacteriol. 176:6688–6696.

Schurr, M. J., H. Yu, N. Boucher, and V. Deretic. (1995) Multiple promoters and induction by heat shock of the gen encoding the alternative sigma factor AlgU ($\sigma^E$) which controls mucoidy in cystic fibrosis isolates of *Pseudomonus aeruginosa. J. Bacteriol.* 177:5670–5679.

Plorde, J. J., (1994), *Sherris Medical Microbiology,* p 401–415, Ryan, K. J. (ed) Appleton and Lange Press, Norwalk, Conn.

Gross, C. A., Lonetto, M., and Losick, R., (1992) *Transciptional Regulation,* p 129–176, Cold Spring Harbor Laboratory Press, McKnight, S. L. and Yamamoto, K. R. (eds).

von Hippel, P. H., Yager, T. D., Gill, S. C. (1992) p 179–201, *Transciptional Regulation,* Cold Spring Harbor Laboratory Press, McKnight, S. L. and Yamamoto, K. R. (eds).

What is claimed is:

1. An isolated, purified DNA, wherein said DNA has a sequence selected from the group consisting of the sequence shown in SEQ. ID. NO. 1 and sequence conservative variants thereof.

2. A DNA vector comprising the DNA of claim 1 operably linked to a transcription regulatory element.

3. A cell comprising a DNA vector as defined in claim 2, wherein said cell is selected from the group consisting of bacterial, fungal, plant, insect, and mammalian cells.

4. A cell as defined in claim 3, wherein said cell is bacterial cell.

* * * * *

SEQUENCE LISTING

<160> NUMBER OF SEQ ID NOS: 9

<210> SEQ ID NO 1
<211> LENGTH: 874
<212> TYPE: DNA
<213> ORGANISM: Mycobacteria tuberculosis

<400> SEQUENCE: 1
gtaacgttgg agatatcgcc gtcgatgaca atgcaagggg aacgtctcga cgctgtggtt 60
gcggaggccg tggcaggaga ccggaacgcg cttcgggagg tgctggagac catccgcccg 120
atcgtcgtgc gatattgccg agcgcgagtc ggcacggtcg agcggagcgg cctgtcagca 180
gatgacgtgg cacaggaggt gtgcttggcc accataacgg cgctgccgcg ctatcgggac 240
cgcggccggc cattcctggc gtttctgtac ggcatcgcgg cgcacaaggt tgccgacgcc 300
catcgggcag ccggccgtga ccgggcctat cccgccgaaa cgcttcctga gcgctggtca 360
gccgacgccg gcccggagca gatggccatc gaggccgatt cggtcacccg gatgaacgaa 420
ttgcttgaga tcttgccggc caagcaacgc gagatcctca ttctgcgtgt tgtcgtcggc 480
ctgtccgcgg aagagaccgc cgccgccgtc ggcagcacca cgggggcggt ccgggtggcc 540
caacaccgtg cacttcagcg gctgaaggac gaaattgttg cggcaggtga ctatgcgtga 600
atttggtaat ccccttggcg atcggccgcc attggatgag ctggcccgca ccgatctgct 660
gctcgacgca ctcgccgaac gggaggaggt tgacttcgcg gatcctcgcg atgacgcgtt 720
ggccgccctg ctcggacagt ggcgcgacga cttgaggtgg ccgccggcca gtgccctggt 780
ttcacaggac gaggccgtcg ccgcgttgcg cgccggggta gcgcaacggc gacgggctcg 840
tcgcagcctg gcggccgtcg ggtcggtggc cgcg 874

<210> SEQ ID NO 2
<211> LENGTH: 224
<212> TYPE: PRT
<213> ORGANISM: Mycobacteria tuberculosis

<400> SEQUENCE: 2

Met Leu Ala Tyr Arg Leu Lys Arg Gly Trp Ala Val Met Val Asp Pro
1 5 10 15

Gly Val Ser Pro Gly Cys Val Arg Phe Val Thr Leu Glu Ile Ser Pro
20 25 30

Ser Met Thr Met Gln Gly Glu Arg Leu Asp Ala Val Val Ala Glu Ala
35 40 45

-continued

```
Val Ala Gly Asp Arg Asn Ala Leu Arg Glu Val Leu Glu Thr Ile Arg
    50                  55                  60

Pro Ile Val Val Arg Tyr Cys Arg Ala Arg Val Gly Thr Val Glu Arg
65                  70                  75                  80

Ser Gly Leu Ser Ala Asp Asp Val Ala Gln Glu Val Cys Leu Ala Thr
                85                  90                  95

Ile Thr Ala Leu Pro Arg Tyr Arg Asp Arg Gly Arg Pro Phe Leu Ala
            100                 105                 110

Phe Leu Tyr Gly Ile Ala Ala His Lys Val Ala Asp Ala His Arg Ala
        115                 120                 125

Ala Gly Arg Asp Arg Ala Tyr Pro Ala Glu Thr Leu Pro Glu Arg Trp
    130                 135                 140

Ser Ala Asp Ala Gly Pro Glu Gln Met Ala Ile Glu Ala Asp Ser Val
145                 150                 155                 160

Thr Arg Met Asn Glu Leu Leu Glu Ile Leu Pro Ala Lys Gln Arg Glu
                165                 170                 175

Ile Leu Ile Leu Arg Val Val Val Gly Leu Ser Ala Glu Glu Thr Ala
            180                 185                 190

Ala Ala Val Gly Ser Thr Thr Gly Ala Val Arg Val Ala Gln His Arg
        195                 200                 205

Ala Leu Gln Arg Leu Lys Asp Glu Ile Val Ala Ala Gly Asp Tyr Ala
    210                 215                 220


<210> SEQ ID NO 3
<211> LENGTH: 177
<212> TYPE: PRT
<213> ORGANISM: Streptomyces coelicolor

<400> SEQUENCE: 3

Met Gly Glu Val Leu Glu Phe Glu Glu Tyr Val Arg Thr Arg Gln Asp
 1               5                  10                  15

Ala Leu Leu Arg Ser Ala Arg Arg Leu Val Pro Asp Pro Val Asp Ala
            20                  25                  30

Gln Asp Leu Leu Gln Thr Ala Leu Ala Arg Thr Tyr Gly Arg Trp Glu
        35                  40                  45

Thr Ile Glu Asp Lys Arg Leu Ala Asp Ala Tyr Leu Arg Arg Val Met
    50                  55                  60

Ile Asn Thr Arg Thr Glu Trp Trp Arg Ala Arg Lys Leu Glu Glu Val
65                  70                  75                  80

Pro Thr Glu Gln Leu Pro Glu Ser Pro Met Asp Asp Ala Thr Glu Gln
                85                  90                  95

His Ala Asp Arg Ala Leu Leu Met Asp Val Leu Lys Val Leu Ala Pro
            100                 105                 110

Lys Gln Arg Ser Val Val Val Leu Arg His Trp Glu Gln Met Ser Thr
        115                 120                 125

Glu Glu Thr Ala Ala Ala Leu Gly Met Ser Ala Gly Thr Val Lys Ser
    130                 135                 140

Thr Leu His Arg Ala Leu Ala Arg Leu Arg Glu Glu Leu Val Ala Arg
145                 150                 155                 160

Asp Leu Asp Ala Arg Ala Leu Glu Arg Glu Glu Arg Glu Arg Cys Ala
                165                 170                 175

Ala


<210> SEQ ID NO 4
<211> LENGTH: 193
```

-continued

<212> TYPE: PRT
<213> ORGANISM: Pseudomonas aeruginosa

<400> SEQUENCE: 4

```
Met Leu Thr Gln Glu Gln Asp Gln Gln Leu Val Glu Arg Val Gln Arg
 1               5                  10                  15

Gly Asp Lys Arg Ala Phe Asp Leu Leu Val Leu Lys Tyr Gln His Lys
            20                  25                  30

Ile Leu Gly Leu Ile Val Arg Phe Val His Asp Ala Gln Glu Ala Gln
        35                  40                  45

Asp Val Ala Gln Glu Ala Phe Ile Lys Ala Tyr Arg Ala Leu Gly Asn
    50                  55                  60

Phe Arg Gly Asp Ser Ala Phe Tyr Thr Trp Leu Tyr Arg Ile Ala Ile
65                  70                  75                  80

Asn Thr Ala Lys Asn His Leu Val Ala Arg Gly Arg Arg Pro Pro Asp
                85                  90                  95

Ser Asp Val Thr Ala Glu Asp Ala Glu Phe Phe Glu Gly Asp His Ala
            100                 105                 110

Leu Lys Asp Ile Glu Ser Pro Glu Arg Ala Met Leu Arg Asp Glu Ile
        115                 120                 125

Glu Ala Thr Val His Gln Thr Ile Gln Gln Leu Pro Glu Asp Leu Arg
    130                 135                 140

Thr Ala Leu Thr Leu Arg Glu Phe Glu Gly Leu Ser Tyr Glu Asp Ile
145                 150                 155                 160

Ala Thr Val Met Gln Cys Pro Val Gly Thr Val Arg Ser Arg Ile Phe
                165                 170                 175

Arg Ala Arg Glu Ala Ile Asp Lys Ala Leu Gln Pro Leu Leu Arg Glu
            180                 185                 190

Ala
```

<210> SEQ ID NO 5
<211> LENGTH: 191
<212> TYPE: PRT
<213> ORGANISM: Escherichia coli

<400> SEQUENCE: 5

```
Met Ser Glu Gln Leu Thr Asp Gln Val Leu Val Glu Arg Val Gln Lys
 1               5                  10                  15

Gly Asp Gln Lys Ala Phe Asn Leu Leu Val Val Arg Tyr Gln His Lys
            20                  25                  30

Val Ala Ser Leu Val Ser Arg Tyr Val Pro Ser Gly Asp Val Pro Asp
        35                  40                  45

Val Val Gln Glu Ala Phe Ile Lys Ala Tyr Arg Ala Leu Asp Ser Phe
    50                  55                  60

Arg Gly Asp Ser Ala Phe Tyr Thr Trp Leu Tyr Arg Ile Ala Val Asn
65                  70                  75                  80

Thr Ala Lys Asn Tyr Leu Val Ala Gln Gly Arg Arg Pro Pro Ser Ser
                85                  90                  95

Asp Val Asp Ala Ile Glu Ala Glu Asn Phe Glu Ser Gly Gly Ala Leu
            100                 105                 110

Lys Glu Ile Ser Asn Pro Glu Asn Leu Met Leu Ser Glu Glu Leu Arg
        115                 120                 125

Gln Ile Val Phe Arg Thr Ile Glu Ser Leu Pro Glu Asp Leu Arg Met
    130                 135                 140

Ala Ile Thr Leu Arg Glu Leu Asp Gly Leu Ser Tyr Glu Glu Ile Ala
```

-continued

```
145                 150                 155                 160

Ala Ile Met Asp Cys Pro Val Gly Thr Val Arg Ser Arg Ile Phe Arg
                165                 170                 175

Ala Arg Glu Ala Ile Asp Asn Lys Val Gln Pro Leu Ile Arg Arg
            180                 185                 190


<210> SEQ ID NO 6
<211> LENGTH: 144
<212> TYPE: PRT
<213> ORGANISM: Haemophilus influenzae

<400> SEQUENCE: 6

Phe Leu Ser Ala Phe Lys Asn Leu Ala Asn Phe Lys Arg Gln Ser Ala
 1               5                  10                  15

Phe Lys Thr Trp Ile Phe Ala Ile Leu Lys Asn Lys Ile Ile Asp Tyr
            20                  25                  30

Leu Arg Gln Lys Gly Arg Phe Val Leu Glu Ser Glu Leu Glu Asp Glu
        35                  40                  45

Asn Thr Asn Asn Ser Phe Phe Asp Glu Lys Gly His Trp Lys Pro Glu
    50                  55                  60

Tyr His Pro Ser Glu Leu Gln Gly Glu Glu Glu Thr Val Tyr Ser Asp
65                  70                  75                  80

Glu Phe Trp Leu Ile Phe Glu Thr Cys Leu Asn Cys Leu Pro Ala Lys
                85                  90                  95

Gln Ala Lys Ile Phe Met Met Arg Glu Phe Leu Glu Leu Ser Ser Glu
            100                 105                 110

Glu Ile Cys Gln Glu Thr His Leu Thr Ser Ser Asn Leu His Thr Thr
        115                 120                 125

Leu Tyr Arg Ala Arg Leu Gln Leu Gln Asn Cys Leu Ser Lys Lys Leu
    130                 135                 140


<210> SEQ ID NO 7
<211> LENGTH: 30
<212> TYPE: DNA
<213> ORGANISM: Mycobacteria leprae

<400> SEQUENCE: 7

atgaacgaac tgctcgagat cttgcctgcc                                        30


<210> SEQ ID NO 8
<211> LENGTH: 30
<212> TYPE: DNA
<213> ORGANISM: Mycobacteria leprae

<400> SEQUENCE: 8

tcacccgccg cgacgatctc ggacgtcaac                                        30


<210> SEQ ID NO 9
<211> LENGTH: 33
<212> TYPE: DNA
<213> ORGANISM: Artificial Sequence
<220> FEATURE:
<223> OTHER INFORMATION: Sigma promoter consensus sequence
<223> OTHER INFORMATION: n can be any base
<223> OTHER INFORMATION: some n can be missing such that:
<223> OTHER INFORMATION: there can be one less n at the span from
      positions 7-23,
<223> OTHER INFORMATION: generating a span of n from positions 7-22;
      and there
<223> OTHER INFORMATION: can be 1-4 less bases at the span from
      positions 13-17,
<223> OTHER INFORMATION: such that there are 1-5 n starting at position
```

-continued

```
      13
<223> OTHER INFORMATION: generating a nucleotide with n at position 13;
<223> OTHER INFORMATION: n from positions 13-14: n from positions 13-15;
<223> OTHER INFORMATION: n from positions 13-16; or n from positions
      13-17.

<400> SEQUENCE: 9

gaacttnnnn nnnnnnnnnn nnntctgann nnn                                33
```